United States Patent [19]
Rajotte et al.

[11] Patent Number: 5,906,101
[45] Date of Patent: May 25, 1999

[54] DEWAR FLASK-COMPATIBLE STORAGE SYSTEM AND METHOD OF USE THEREOF

[75] Inventors: Ray V. Rajotte, Edmonton, Canada; Jonathan R. T. Lakey, Indianapolis, Ind.

[73] Assignee: University of Alberta, Edmonton, Canada

[21] Appl. No.: 08/961,500

[22] Filed: Oct. 30, 1997

[51] Int. Cl.[6] .................................................. F25B 19/00
[52] U.S. Cl. ................................................. 62/51.1; 62/78
[58] Field of Search ...................................... 62/51.1, 78

[56] References Cited

U.S. PATENT DOCUMENTS

| | | | |
|---|---|---|---|
| 4,090,374 | 5/1978 | Faust et al. | 62/341 |
| 4,314,450 | 2/1982 | Pelloux-Gervais | 62/51.1 |
| 4,388,814 | 6/1983 | Schilling | 62/51.1 |
| 4,712,607 | 12/1987 | Lindemans et al. | 62/51.1 |
| 5,321,955 | 6/1994 | Leonard | 62/51.1 |
| 5,419,143 | 5/1995 | Leonard et al. | 62/51.1 |
| 5,469,712 | 11/1995 | Sitte et al. | 62/51.1 |
| 5,638,686 | 6/1997 | Coelho et al. | 62/51.1 |

Primary Examiner—Ronald Capossela
Attorney, Agent, or Firm—Nikaido Marmelstein Murray & Oram LLP

[57] ABSTRACT

A system for storing a plurality of cryopreservable samples is provided, comprising a liquid nitrogen Dewar flask having a substantially circular opening of diameter X defined therein, the Dewar flask containing therein a plurality of Dewar flask-compatible storage racks, each storage rack comprising at least one substantially rectangular container, having a first set of opposite sides in substantially perpendicular relationship with a second set of opposite sides, the first set of opposite sides and the second set of opposite sides defining an inner space therebetween, and a plurality of strips, located in the inner space and each in contact with at least one side, formed in substantially parallel relationship with the first set of opposite sides, the plurality of strips forming a plurality of storage slots in the inner space, wherein at least one of the plurality of storage slots contains a cassette containing therein a cryopreservable sample. The plurality of storage racks are arranged in the Dewar flask such that a circle intersecting at least two of the plurality of storage racks located in the Dewar flask has a diameter which is greater than the diameter X of the opening. A method of storing cryopreservable samples is also provided.

5 Claims, 3 Drawing Sheets

DEWAR FLASK-COMPATIBLE STORAGE SYSTEM AND METHOD OF USE THEREOF

BACKGROUND OF THE INVENTION

The present invention relates to a liquid nitrogen Dewar flask-compatible storage rack suitable for storing cryopreservable samples. The present invention also relates to a system for storing cryopreservable samples, along with a method of storing a cryopreservable sample in a liquid nitrogen-containing Dewar flask.

DESCRIPTION OF THE RELATED ART

The present invention relates to storage of cryopreservable samples. Presently, there is no existing means to effectively store cryopreservable samples in a large mouth liquid nitrogen-containing Dewar flask and maintain the desired quality control with easy retrievability of samples and low cost.

Previously, when cryopreservable samples were placed in a liquid nitrogen-containing Dewar flask, the samples were not easy to retrieve, The samples had to be taken out of the Dewar flask and sorted through by hand in order to find the desired sample. This lead to wasted time and effort, along with the chance that cryopreservable samples would be misplaced during the sorting process, or would partially defrost or spoil. A system was needed whereby cryopreservable samples could be easily located and retrieved in little time, with minimized chance of misplacement or accidental spoilage of a sample.

Large capacity low-temperature freezer systems are available, which increase the ease of location of a sample, and minimize the chance of accidental misplacement or spoilage of a sample. However, these large freezer systems are costly. First, there is the initial high purchase costs associated with such a system. In addition, there is a high upkeep cost for maintaining liquid nitrogen in the system. These large freezer systems have high evaporation rates for liquid nitrogen, and are therefore ineffective at maintaining proper inventory control of the cryopreservable samples without constant supervision. Thus, there is a long felt need for a system for storing cryopreservable samples which minimizes the problems associated with such large freezer systems, and this need is especially great for smaller research centers, blood and tissue banks and hospitals.

The object of the present invention is to eliminate or minimize the problems associated with prior art systems for storing cryopreservable samples.

SUMMARY OF THE INVENTION

The present invention, therefore, is directed to a liquid nitrogen Dewar flask-compatible storage rack suitable for storing cryopreservable samples, the storage rack comprising:

at least one substantially rectangular container, having a first set of opposite sides in substantially perpendicular relationship with a second set of opposite sides, the first set of opposite sides and the second set of opposite sides defining an inner space therebetween, a plurality of strips, located in the inner space and each in contact with at least one side, formed in substantially parallel relationship with the first set of opposite sides, the plurality of strips forming a plurality of storage slots in the inner space, each of the plurality of storage slots capable of receiving a cassette containing a cryopreservable sample, engaging means for removably engaging the storage rack with the liquid nitrogen Dewar flask, and correlating means for correlating each of the plurality of storage slots with the cassette received therein.

The present invention is also directed to a system for storing a plurality of cryopreservable samples, comprising a liquid nitrogen Dewar flask having a substantially circular opening of diameter X defined therein, the Dewar flask containing therein a plurality of Dewar flask-compatible storage racks, each storage rack comprising:

at least one substantially rectangular container, having a first set of opposite sides in substantially perpendicular relationship with a second set of opposite sides, the first set of opposite sides and the second set of opposite sides defining an inner space therebetween, and a plurality of strips, located in the inner space and each in contact with at least one side, formed in substantially parallel relationship with the first set of opposite sides, the plurality of strips forming a plurality of storage slots in the inner space, wherein at least one of the plurality of storage slots contains a cassette containing therein a cryopreservable sample, wherein the plurality of storage racks are arranged in the Dewar flask such that a circle intersecting at least two of the plurality of storage racks located in the Dewar flask has a diameter which is greater than the diameter X of the opening.

Another system of the invention for storing a plurality of cryopreservable samples, comprises a liquid nitrogen Dewar flask having an opening defined therein, the Dewar flask containing therein a plurality of Dewar flask-compatible storage racks, each storage rack comprising:

at least one substantially rectangular container, having a first set of opposite sides in substantially perpendicular relationship with a second set of opposite sides, the first set of opposite sides and the second set of opposite sides defining an inner space therebetween, and a plurality of strips, located in the inner space and each in contact with at least one side, formed in substantially parallel relationship with the first set of opposite sides, the plurality of strips forming a plurality of storage slots in the inner space, wherein at least one of the plurality of storage slots contains a cassette containing therein a cryopreservable sample, wherein each of the plurality of storage racks are arranged at distances from each other in the Dewar flask to form an assembly, such that the plurality of storage racks cannot be withdrawn from the Dewar flask through the opening without disturbing the relative distances between the plurality of storage racks in the assembly.

Another subject matter of the present invention is a liquid nitrogen Dewar flask-compatible storage kit suitable for storing a cryopreservable sample, comprising:

a storage rack, comprising at least one substantially rectangular container, having a first set of opposite sides in substantially perpendicular relationship with a second set of opposite sides, the first set of opposite sides and the second set of opposite sides defining an inner space therebetween, and a plurality of strips, located in the inner space and each in contact with at least one side, formed in substantially parallel relationship with the first set of opposite sides, the plurality of strips forming a plurality of storage slots in the inner space; and a cassette, located in one of the plurality of storage slots, containing a cryopreservable sample.

Still another subject matter of the present invention is a method of storing a cryopreservable sample in a liquid nitrogen Dewar flask, the method comprising:

providing a liquid nitrogen Dewar flask having a substantially circular opening of diameter X defined therein, providing a plurality of Dewar flask-compatible storage racks, each storage rack comprising:

at least one substantially rectangular container, having a first set of opposite sides in substantially perpendicular relationship with a second set of opposite sides, the first set of opposite sides and the second set of opposite sides defining an inner space therebetween, and a plurality of strips, located in the inner space and each in contact with at least one side, formed in substantially parallel relationship with the first set of opposite sides, the plurality of strips forming a plurality of storage slots in the inner space, thereafter introducing at least one cassette containing a cryopreservable sample into each storage rack via one of the plurality of storage slots, placing liquid nitrogen into the liquid nitrogen Dewar flask, and before or after said placing step, introducing the plurality of storage racks each having the at least one cassette located therein into the liquid nitrogen Dewar flask to store the cryopreservable sample, wherein the plurality of storage racks are arranged in the Dewar flask such that a circle intersecting at least two of the plurality of storage racks located in the Dewar flask has a diameter which is greater than the diameter X of the opening.

DESCRIPTION OF THE PREFERRED EMBODIMENTS

Figure 1:
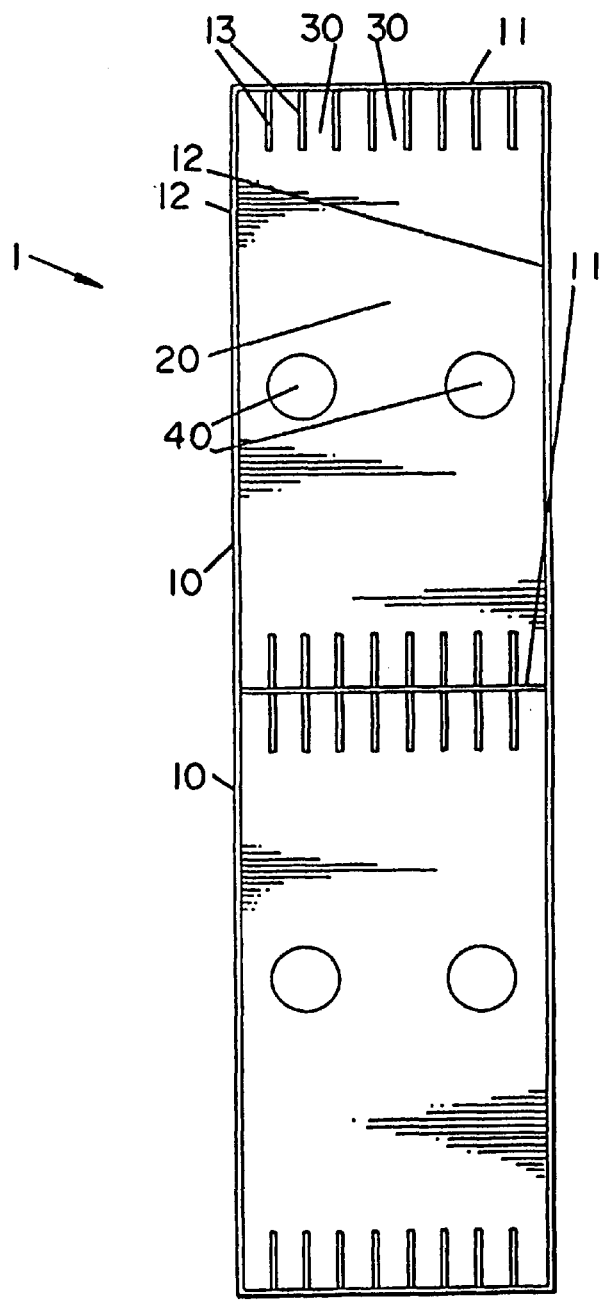
FIG 1. is a frontal view of a preferred embodiment of the storage rack of the present invention.
Figure 2:
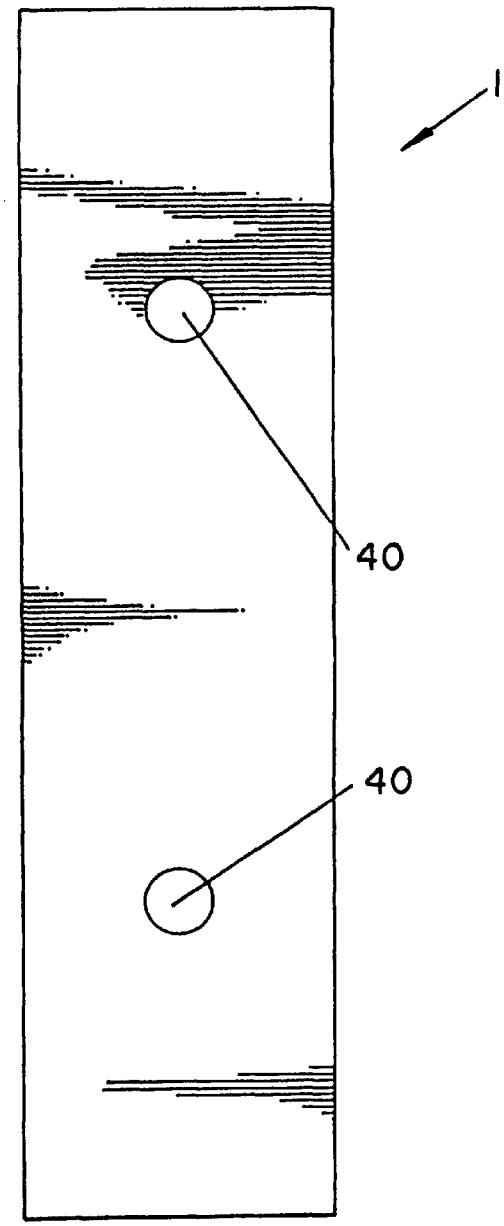
FIG. 2 is a side view of the storage rack of FIG. 1.

Referring to FIGS. 1 and 2, a preferred liquid nitrogen Dewar flask-compatible storage rack 1 is shown. The storage rack according to FIGS. 1 and 2 has two substantially rectangular containers 10. The structure of each substantially rectangular container 10 according to the embodiment shown is the same, so description of only one container is believed necessary. The container 10 has two sets of opposite sides 11 and 12 which are in substantially perpendicular relationship with one another. The two sets of opposite sides 11 and 12 define an inner space 20 therebetween. Located within the inner space 20 is a plurality of strips 13, each of which in the embodiment shown is in contact with one side of the container 10, although it is also possible to have each of the plurality of strips being in contact with two opposite sides of the container 10 (i.e., forming a continuous strip from one side of the container to the other opposite side). It is important to note that, while the plurality of strips in the embodiment shown in FIG. 1 are formed vertically in the inner space, the present invention also includes a plurality of strips that are formed horizontally in the inner space.

The plurality of strips 13 form a plurality of storage slots 30 in the inner space. Each of the plurality of storage slots 30 is capable of receiving a cassette containing a cryopreservable sample.

The storage rack 1 preferably contains at least one, and more preferably a plurality of holes 40 extending from the inner space of the container 10 to outside the container 10 to allow for drainage of liquid nitrogen from the inner space when the storage rack 1 is removed from a liquid nitrogen-containing Dewar flask.

Figure 5:
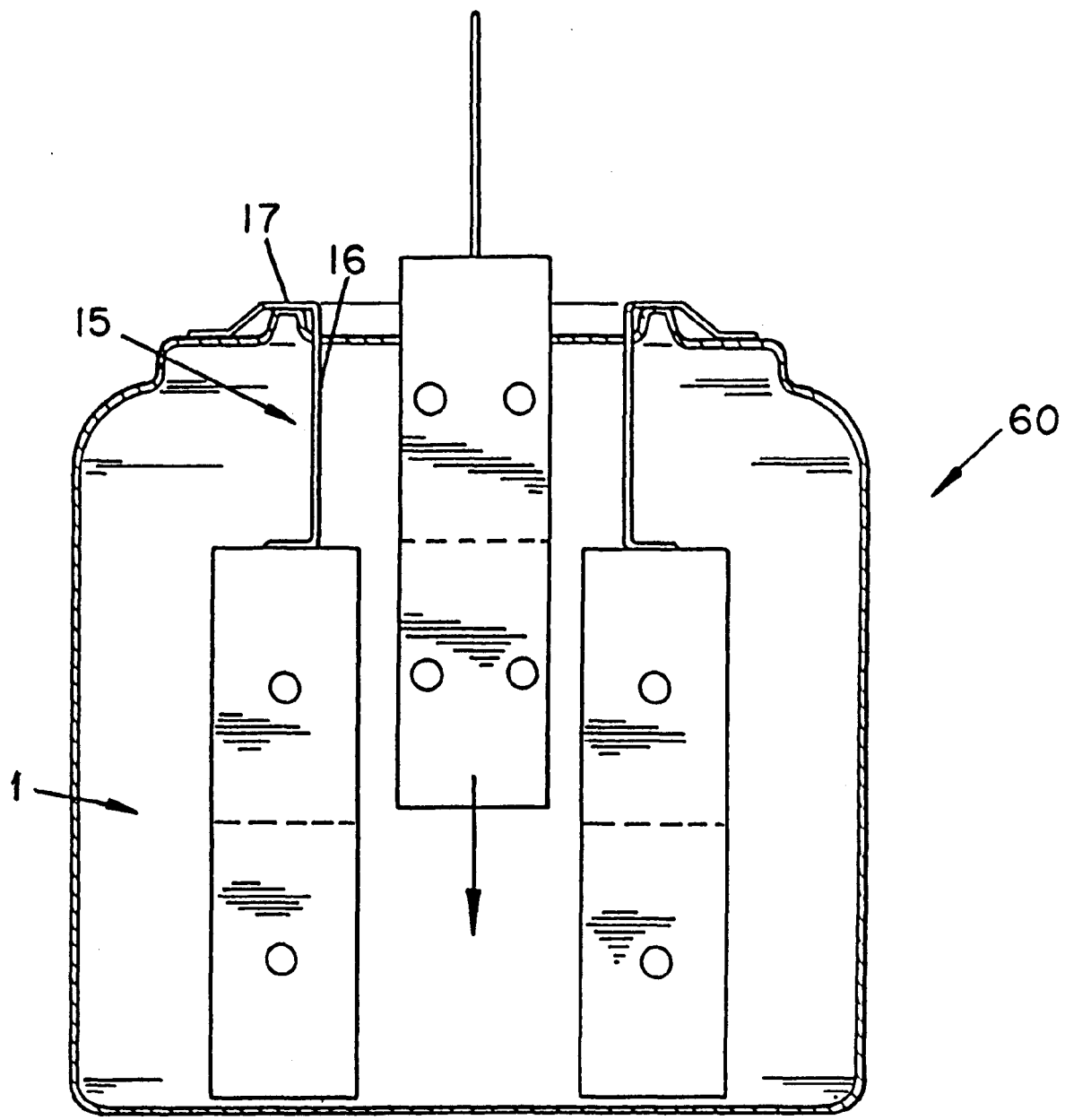
FIG. 5 is a cross-sectional view of a liquid nitrogen Dewar flask having a plurality of storage racks introduced therein.

Referring to FIG. 5, a liquid nitrogen Dewar flask 60 having a plurality of storage racks 1 introduced therein is shown. Each of the storage racks 1 in the embodiment shown in FIG. 5 is provided with engaging means 15 (in this embodiment, a substantially J-shaped hook 17 integral with a shaft 16), located at a side of the container 10 for removably engaging the storage rack 1 with the liquid nitrogen Dewar flask 60. The engaging means can be of any size or shape, and can be located at or proximate one side of the container 10, as long as the engaging means can provide the function of reversibly engaging the storage rack with the liquid nitrogen Dewar flask. As is clear from FIG. 5, the liquid nitrogen Dewar flask has a substantially circular opening of a certain diameter defined therein. The plurality of storage racks are arranged in the Dewar flask such that an imaginary circle drawn to intersect at least two of the plurality of storage racks located in the Dewar flask has a diameter which is greater than the diameter of the opening of the Dewar flask. Put another way, each of the plurality of storage racks are arranged at distances from each other in the Dewar flask to form an assembly. Once the assembly has been formed, the plurality of storage racks cannot be withdrawn from the Dewar flask through the opening without disturbing the relative distances between the plurality of storage racks in the assembly.

Such an arrangement of the plurality of storage racks in the Dewar flask has advantages over known storage methods in that a greater amount of samples can be stored in one particular Dewar flask. This saves expense because it is a more efficient use of space and therefore requires fewer Dewar flasks and less liquid nitrogen.

Figure 4:
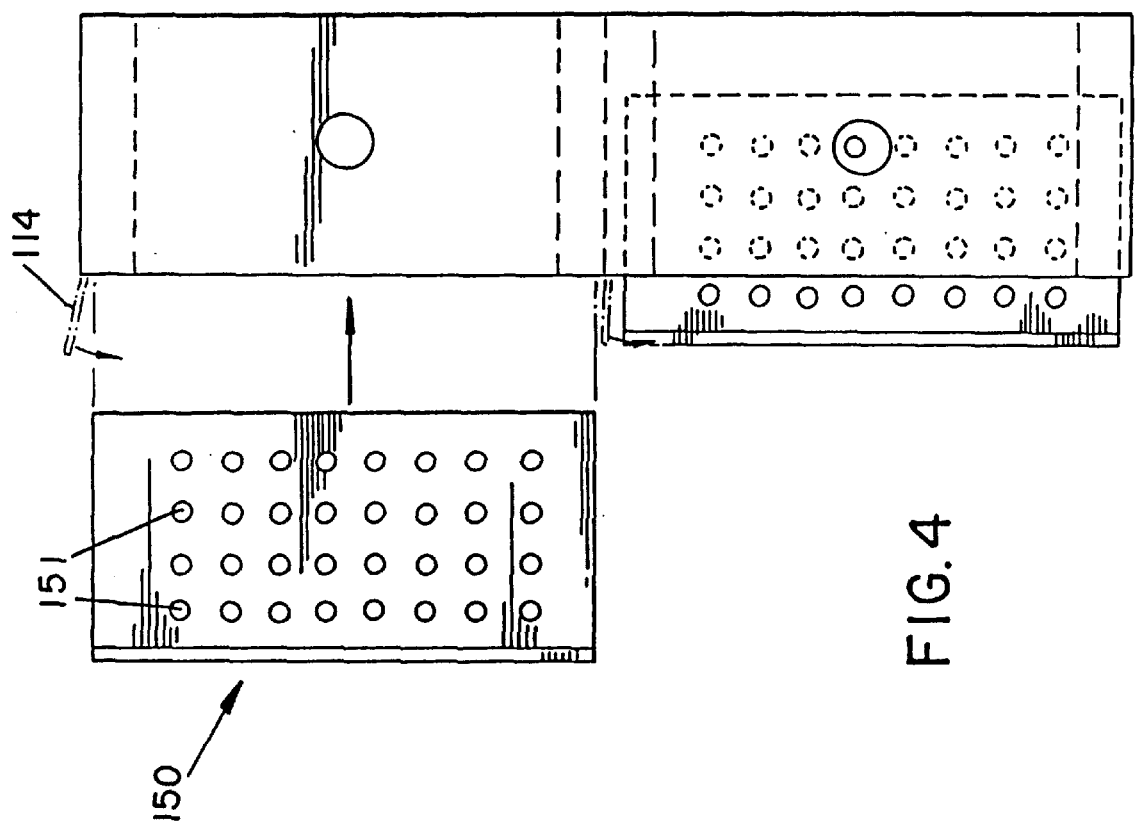
FIG. 4 is a side view of the storage rack of FIG. 3, showing how the plurality of cassettes are received therein.
Figure 3:
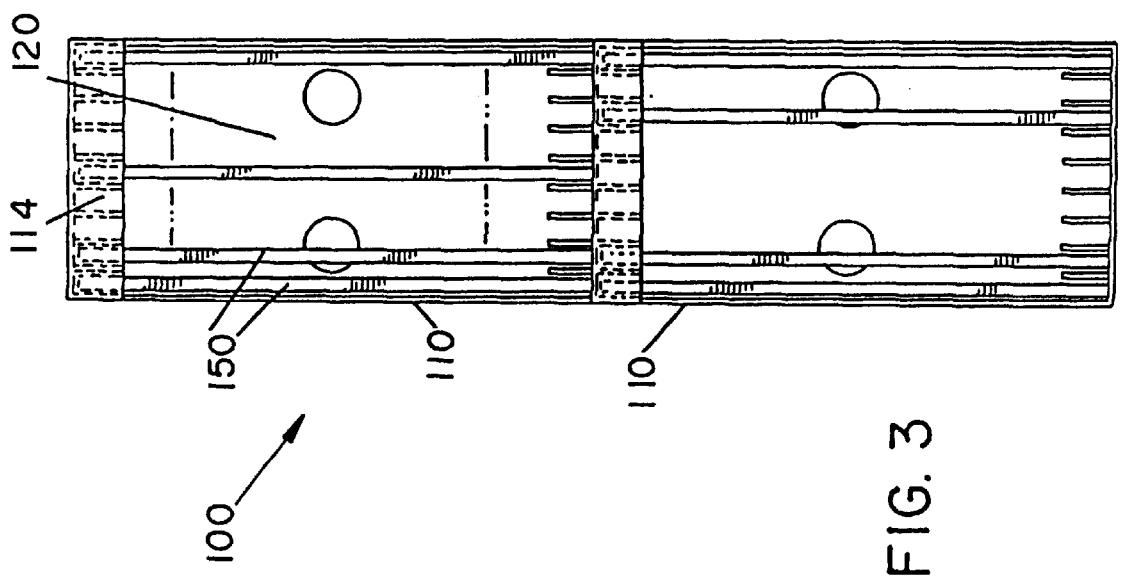
FIG. 3 is a frontal view of another preferred embodiment of the storage rack of the present invention, having a plurality of cassettes received therein.

FIGS. 3 and 4 show another embodiment of a storage rack 100 of the present invention, having a plurality of cassettes 150 received therein. The cassettes 150 preferably contain holes 151 therein, for allowing liquid nitrogen to penetrate the cassettes. The storage rack 100 shown in FIGS. 3 and 4 has preventing means 114 for preventing the cassettes 150 from protruding from the inner space 120 to outside the container 110. Preferably, the preventing means comprises a hinge attached to one side of the container 110, and at least partially covering the periphery of the inner space 120, as is clear from FIGS. 3 and 4. However, the preventing means can be any device which prevents the cassettes from protruding from the inner space of the container, such as a bar, metal curtain, door, etc.

The storage rack of the present invention also preferably has correlating means for correlating each of the plurality of storage slots with the cassette received therein. The correlating means preferably comprises coded punches which label the plurality of storage slots. The coded punches could be located on the outer or inner space of the container, on the storage slots, or on the preventing means. The coded punches may take the form of raised or depressed bumps or numerals, which do not go through the surface, or piercings which go through the surface. Other correlating means are also encompassed by the present invention, such as tags, color coding, stamping, etc.

The storage rack is preferably formed of stainless steel, although any material which can withstand the temperatures associated with liquid nitrogen are equally suitable. The storage rack can be manufactured by standard means, such as welding, which are known in the manufacturing art.

The present invention is suitable for storing a wide range of cryopreservable samples, such as pancreatic islets, bone marrow, a tissue or cell system, blood, blood cell products, placental cord blood, skin and heart valves. There is no limitation to the size or character of a sample that can be stored, as long as the sample can fit within a cassette to be received in the storage rack. Presently, the size of the cassette is controlled by the opening of the mouth of the liquid nitrogen Dewar flask, since the cassette must be able to fit within the Dewar flask mouth.

Preferably, the cryopreservable sample is contained in a freezer bag, and the freezer bag is contained within the cassette. This insures that the integrity of the cryopreservable sample is maintained, and also protects against contamination. The size of the freezer bag is limited by the size of the cassette, and preferably, the bag should snugly fit within the cassette to insure uniform cooling of the sample. For example, if the freezer bag is 5 mm in width when filled (which is common for 100 ml freezer bags), the width of the cassette should be about ½ in. There is no limit to the size of the freezer bags and cassettes which can be used in the present invention, except the size of the liquid nitrogen Dewar flask itself.

The present invention also includes a method of storing a plurality of cryopreservable samples in a liquid nitrogen Dewar flask. The method includes providing a liquid nitrogen Dewar flask having a substantially circular opening of diameter X defined therein, providing a plurality of Dewar flask-compatible storage racks as described above, thereafter introducing at least one cassette containing a cryopreservable sample into each storage rack via one of the plurality of storage slots, placing liquid nitrogen into the liquid nitrogen Dewar flask, and (before or after the placing step), introducing the plurality of storage racks each having the at least one cassette located therein into the liquid nitrogen Dewar flask to store the cryopreservable sample. Preferably, the plurality of storage racks are arranged in the Dewar flask such that a circle intersecting at least two of the plurality of storage racks located in the Dewar flask has a diameter which is greater than the diameter X of the opening.

The storage rack system, and method of the present invention is useful for the short- or long-term storage of cryopreservabe samples, and provides the advantages over previous systems discussed above. Those of skill in the art will appreciate that certain modifications can be made within the spirit of the invention as herein described. The preferred embodiments of the present invention should not be taken as limiting the scope of the invention in any way, the true scope of the invention to be determined only by the following claims.

We claim:

1. A system for storing a plurality of cryopreservable samples, comprising a liquid nitrogen Dewar flask having a substantially circular opening of diameter X defined therein, the Dewar flask containing therein a plurality of Dewar flask-compatible storage racks, each storage rack comprising:

at least one substantially rectangular container, having a first set of opposite sides in substantially perpendicular relationship with a second set of opposite sides, the first set of opposite sides and the second set of opposite sides defining an inner space therebetween, and a plurality of strips, located in the inner space and each in contact with at least one side, formed in substantially parallel relationship with the first set of opposite sides, the plurality of strips forming a plurality of storage slots in the inner space, wherein at least one of the plurality of storage slots contains a cassette containing therein a cryopreservable sample, wherein the plurality of storage racks are arranged in the Dewar flask such that a circle intersecting at least two of the plurality of storage racks located in the Dewar flask has a diameter which is greater than the diameter X of the opening.

2. The system of claim 1, wherein the storage rack further comprises engaging means for removably engaging the storage rack with the liquid nitrogen Dewar flask.

3. The system of claim 1, wherein the storage rack further comprises correlating means for correlating each of the plurality of storage slots with the cassette received therein.

4. A method of storing a plurality of cryopreservable samples in a liquid nitrogen Dewar flask, the method comprising:

providing a liquid nitrogen Dewar flask having a substantially circular opening of diameter X defined therein, providing a plurality of Dewar flask-compatible storage racks, each storage rack comprising:

at least one substantially rectangular container, having a first set of opposite sides in substantially perpendicular relationship with a second set of opposite sides, the first set of opposite sides and the second set of opposite sides defining an inner space therebetween, and a plurality of strips, located in the inner space and each in contact with at least one side, formed in substantially parallel relationship with the first set of opposite sides, the plurality of strips forming a plurality of storage slots in the inner space, thereafter introducing at least one cassette containing a cryopreservable sample into each storage rack via one of the plurality of storage slots, placing liquid nitrogen into the liquid nitrogen Dewar flask, and before or after said placing step, introducing the plurality of storage racks each having the at least one cassette located therein into the liquid nitrogen Dewar flask to store the cryopreservable sample, wherein the plurality of storage racks are arranged in the Dewar flask such that a circle intersecting at least two of the plurality of storage racks located in the Dewar flask has a diameter which is greater than the diameter X of the opening.

5. A system for storing a plurality of cryopreservable samples, comprising a liquid nitrogen Dewar flask having an opening defined therein, the Dewar flask containing therein a plurality of Dewar flask-compatible storage racks, each storage rack comprising:

at least one substantially rectangular container, having a first set of opposite sides in substantially perpendicular relationship with a second set of opposite sides, the first set of opposite sides and the second set of opposite sides defining an inner space therebetween, and a plurality of strips, located in the inner space and each in contact with at least one side, formed in substantially parallel relationship with the first set of opposite sides, the plurality of strips forming a plurality of storage slots in the inner space, wherein at least one of the plurality of storage slots contains a cassette containing therein a cryopreservable sample, wherein each of the plurality of storage racks are arranged at distances from each other in the Dewar flask to form an assembly, such that the plurality of storage racks cannot be withdrawn from the Dewar flask through the opening without disturbing the relative distances between the plurality of storage racks in the assembly.

* * * * *